(12) United States Patent
Jahrmarkt et al.

(10) Patent No.: US 6,666,812 B2
(45) Date of Patent: Dec. 23, 2003

(54) RADIOACTIVE THERAPEUTIC SEEDS

(75) Inventors: Scott L. Jahrmarkt, Miami Beach, FL (US); David P. Gordon, Stamford, CT (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 10/281,731

(22) Filed: Oct. 28, 2002

(65) Prior Publication Data

US 2003/0069463 A1 Apr. 10, 2003

Related U.S. Application Data

(63) Continuation of application No. 09/860,405, filed on May 18, 2001, now Pat. No. 6,471,632.

(51) Int. Cl.[7] .......................... A61M 36/00; A61N 5/00
(52) U.S. Cl. .................................................. 600/8
(58) Field of Search ................................. 600/1–8

(56) References Cited

U.S. PATENT DOCUMENTS

| | | | |
|---|---|---|---|
| 3,351,049 A | 11/1967 | Lawrence | 128/1.2 |
| 4,323,055 A | 4/1982 | Kubiatowicz | 128/1.2 |
| 4,510,924 A | 4/1985 | Gray | 128/1.2 |
| 4,697,575 A | 10/1987 | Horowitz | 128/1.2 |
| 4,702,228 A | 10/1987 | Russell, Jr. et al. | 128/1.2 |
| 4,754,745 A | 7/1988 | Horowitz | 128/1.2 |
| 4,763,642 A | 8/1988 | Horowitz | 128/1.2 |
| 4,784,116 A | 11/1988 | Russell, Jr. | 128/1.2 |
| 4,789,501 A | 12/1988 | Day et al. | 252/645 |
| 4,815,449 A | 3/1989 | Horowitz | 600/7 |
| 4,819,618 A | 4/1989 | Liprie | 600/7 |
| 4,891,165 A | 1/1990 | Suthanthiran | 252/633 |
| 4,994,013 A | 2/1991 | Suthanthiran | 600/65 |
| 5,141,487 A | 8/1992 | Liprie | 600/7 |
| 5,163,896 A | 11/1992 | Suthanthiran | 600/8 |
| 5,322,499 A | 6/1994 | Liprie | 600/8 |
| 5,342,283 A | 8/1994 | Good | 600/8 |
| 5,395,300 A | 3/1995 | Liprie | 600/3 |
| 5,405,309 A | 4/1995 | Carden, Jr. | 600/3 |
| 5,460,592 A | 10/1995 | Langton et al. | 600/7 |
| 5,503,614 A | 4/1996 | Liprie | 600/7 |
| 5,713,828 A | 2/1998 | Coniglione | 600/7 |
| 6,007,475 A | 12/1999 | Slater et al. | 600/8 |
| 6,010,446 A | 1/2000 | Grimm | 600/7 |
| 6,016,439 A | 1/2000 | Acker | 600/414 |
| 6,066,083 A | 5/2000 | Slater | 600/8 |
| 6,080,099 A | 6/2000 | Slater et al. | 600/8 |
| 6,099,458 A | 8/2000 | Robertson | 600/8 |
| 6,200,258 B1 | 3/2001 | Slater et al. | 600/8 |
| 6,210,316 B1 | 4/2001 | Slater et al. | 600/8 |
| 6,273,851 B1 | 8/2001 | Slater et al. | 600/8 |
| 6,471,631 B1 | 10/2002 | Slater et al. | 600/8 |
| 6,471,632 B1 * | 10/2002 | Jahrmarkt et al. | 600/8 |

* cited by examiner

*Primary Examiner*—John P. Lacyk
(74) *Attorney, Agent, or Firm*—Gordon & Jacobson, P.C.

(57) ABSTRACT

Radioactive therapeutic seeds include one or more carrier structures each carrying a radioactive isotope, a ceramic spacer or collar member, a metal ring about the ceramic member, and a capsule formed from two tubular parts, each part including a closed end, an open end, and an interior. The open ends of the capsule abut the metal ring and are preferably welded thereto to form a generally uniform capsule wall such that the carrier structure(s) and ceramic member are contained in the interior of the capsule. The ceramic spacer preferably is hollow and a radiopaque or MRI-visible marker extends therethrough. Each of the embodiments is designed to provide a substantially isotropic distribution of radiation.

10 Claims, 3 Drawing Sheets

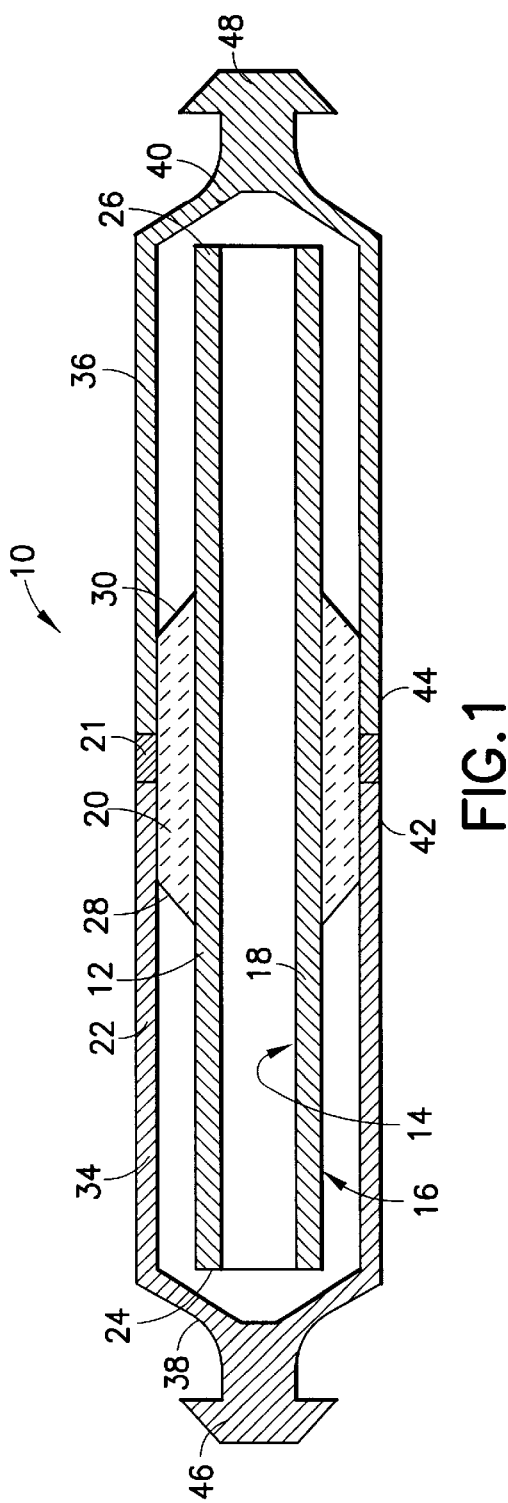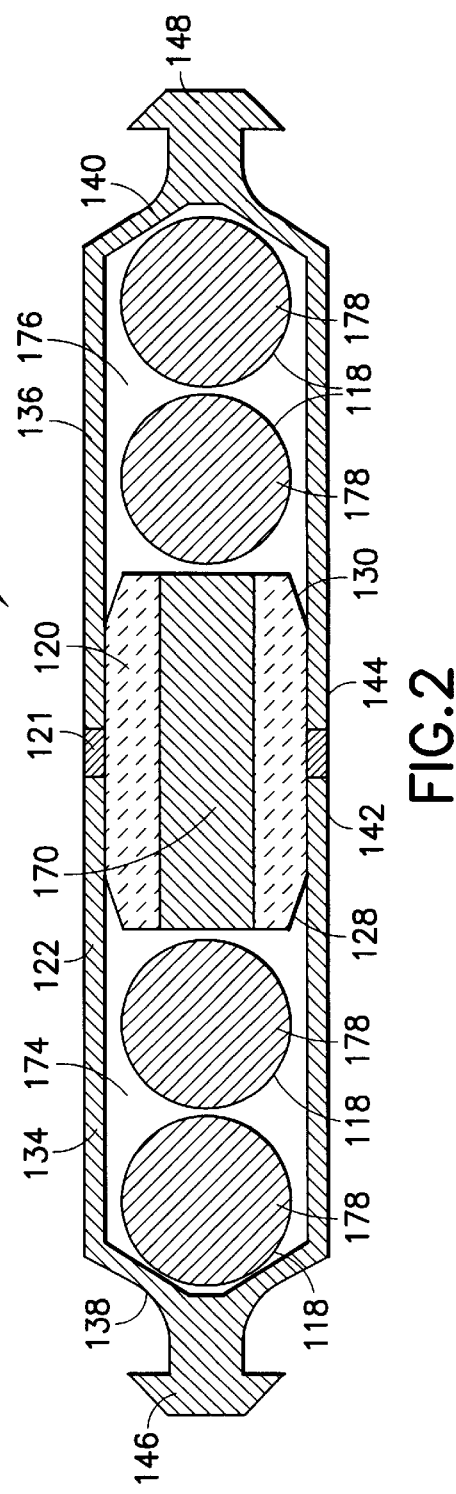

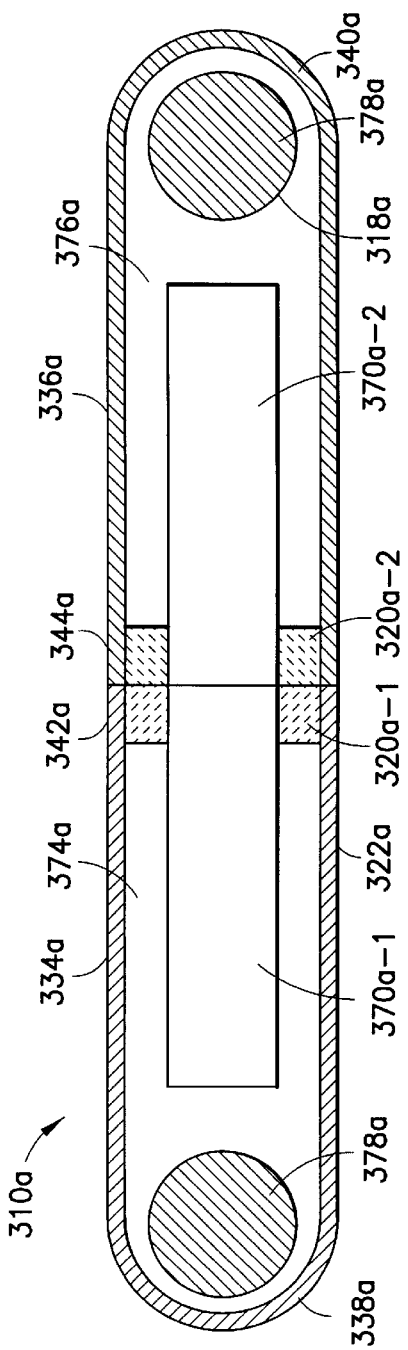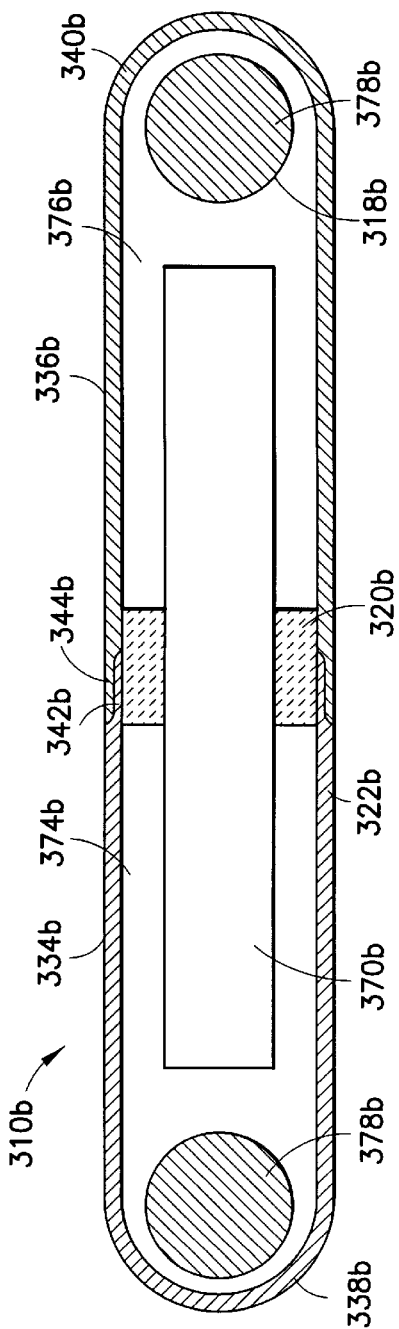
FIG.4a
FIG.4b

RADIOACTIVE THERAPEUTIC SEEDS

This is a continuation of application Ser. No. 09/860,405, filed May 18, 2001 now U.S. Pat. No. 6,471,632.

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of fifty to one hundred tiny capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they are relatively small, typically approximately 0.025 inch in diameter and approximately 0.16 inch long so that they may be implanted using minimally invasive instruments and techniques. Second, the radioactive isotope must be enclosed in a biocompatible protective package since the seeds are typically not removed and will remain in the body for many years. Third, each seed preferably includes a radiopaque (e.g. high Z material) marker so that it can be located at the treatment site with the aid of fluoroscopy. Fourth, the protective package and the radiopaque marker preferably do not cast "shadows" in the irradiation pattern of the isotope. Fifth, the isotope should be evenly distributed within the protective package so as to avoid any "hot spots" of radiation.

The state of the art of radioactive therapeutic seeds is substantially disclosed in several co-owned patents to Slater et al. including U.S. Pat. Nos. 6,007,475, 6,066,083, 6,080,099, 6,200,316, 6,210,316 as well as eight additional U.S. Pat. No. 6,099,458 to Robertson for "Encapsulated Low-Energy Brachytherapy Sources", U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner (s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which substantially do not absorb X-rays. The isotope is coated on a rod shaped carrier made of similar X-ray transparent (e.g. low Z) material and is placed inside the capsule cylinder. The ends of the capsule cylinder are closed by swaging or spinning and soldering or welding. According to a preferred embodiment, Lawrence places a radiopaque marker inside the seed. In one embodiment, the marker is a wire embedded inside the carrier rod. The wire is made of high atomic number material such as gold or tungsten which absorb X-rays.

In 1980, Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination. Thus, the seeds may be placed more accurately at or around the treatment site.

Several years later, Russell, Jr. et al., in U.S. Pat. Nos. 4,707,228 and 4,784,116, explained that the capsule design of Lawrence and Kubiatowicz produces anisotropic angular radiation distribution. According to Russell, Jr. et al., the shell forming techniques used in the Lawrence-type seeds results in large beads of shell material at the ends of the seeds. These beads substantially shield radiation thereby casting shadows in the irradiation pattern of the isotope. Russell, Jr. et al. proposed a new seed design to solve this problem. In particular, Russell, Jr. et al. proposed a seed having a cylindrical container which is sealed with end caps which have a wall thickness that is substantially the same as the wall thickness of the cylindrical container. The end caps are attached to the cylindrical container by welding or crimping.

An alternate solution to the non-uniform radiation pattern of the Lawrence type seeds was proposed by Suthanthiran in U.S. Pat. No. 4,891,165. Suthanthiran's solution was to form a seed capsule from two interfitting sleeves, each having one open end and one closed end. The thickness of the sleeve side walls and their closed ends is such that when the sleeves are interfit in an overlapping manner, the total side wall thickness of the assembled capsule is approximately equal to the end wall thickness.

Other improvements in radioactive therapeutic seeds are disclosed in U.S. Pat. No. 5,405,309 which concerns a safe isotopically pure Pd-103 seed, U.S. Pat. No. 5,713,828 which discloses a hollow tube seed which can be implanted with suture material, and U.S. Pat. No. 6,099,458 which discloses a seeds which are manufactured in a simplified manner which includes placing sources in titanium capsule halves, providing a titanium plug having a marker therein internal the capsule halves, and welding the titanium capsule halves to the titanium plug.

Despite the fact that radioactive therapeutic seeds have been in use for over thirty years and despite the several significant improvements made in these seeds, many concerns still exist regarding their design and construction. For example, while significant attention has been given to the methods by which a cylindrical seed capsule is sealed, it is still difficult to seal such a small cylindrical capsule without adversely affecting the functionality of the seed. Most capsules are sealed at an end using solder which causes a shadow and consequent anisotropic radiation distribution, and while the U.S. Pat. No. 6,200,258 to Slater et al., and U.S. Pat. No. 6,099,458 to Robertson overcome some of these problems, they still suffer from issues regarding thick plugs of titanium around the markers which can affect the isotropic distribution of radiation.

SUMMARY OF THE INVENTION

It is therefore an object of the invention to provide radioactive therapeutic seeds which have a relatively isotropic radiation pattern.

It is also an object of the invention to provide radioactive therapeutic seeds which are easy to manufacture.

It is another object of the invention to provide radioactive therapeutic seeds which can be deployed relatively quickly and easily.

In accord with these objects which will be discussed in detail below, the radioactive therapeutic seeds of the present invention include a substantially radiotransparent cylindrical capsule containing a radioactive isotope and preferably a radiopaque marker. Each of the embodiments is designed to provide a substantially isotropic distribution of radiation. As used herein, the terms "radiotransparent", "radiolucent", "radiotranslucent", and "low Z material" are used interchangeably.

According to a first embodiment of the invention, the isotope is deposited on the outer surface of a hollow radiolucent tube and a ceramic collar having a metal ring centrally located thereon is preferably tightly fit about a central portion of the tube. The capsule comprises two tubular halves, each having a closed end and an open end. The halves of the capsule are positioned over the tube with the open ends of the halves being interference fit with the collar and abutting the metal ring. The capsule halves, typically formed of titanium, are welded to the ring (also typically formed of titanium) to seal the capsule. The ceramic collar protects the contents of the capsule from the heat of welding and is even more radiotransparent than the titanium, and therefore does not affect the radiation pattern of the seed.

According to a second embodiment of the invention, the isotope bearing structure may be one or more radiolucent particles, preferably made from titanium, aluminum or glass, and preferably spherically shaped. The particles are provided with a thin coating of silver to facilitate the adhesion of the isotope thereto. Also provided is a tubular ceramic spacer having an axial radiopaque marker therein and a titanium ring thereon. The titanium ring provides a surface to which the open ends of the two halves of the capsule are butt against and welded.

According to a third embodiment of the invention, the isotope bearing structure is preferably a pair of silver tubes having outer and inner surfaces on which the isotope is provided. One silver tube is positioned in each half of the capsule, and the halves of the capsule are welded about a titanium ring which is fit over a centrally located tubular ceramic spacer. The spacer is preferably provided with a radiopaque marker therein. In addition, the isotope bearing tube is preferably smaller than the interior of each half of the capsule, and additional spacers are preferably provided in each half of the capsule between the tube and the ceramic spacer to prevent relative movement of the tube within the capsule.

In each of the first three embodiments, it is preferred that the ring surrounding the ceramic spacer be made of the same material as the walls of the capsule halves. Depending upon the process of joining the capsule halves, the ring may be the same thickness as the walls of the capsule halves or may have a slightly greater thickness (e.g., up to 0.005 inches thicker) than the capsule halves so that the ring stands proud of the capsule halves, provided that after joining the capsule halves together, the ring is substantially flush with (within a few thousands of an inch) the capsule halves. In addition, in each of the first three embodiments it will be appreciated that the halves of the capsule do not overlap each other and the configuration of the capsule, isotope, and ceramic spacer or collar provide the seed with a highly isotropic distribution of radiation.

According to a fourth embodiment of the invention, the isotope bearing structure may be one or more radiolucent particles, preferably made from titanium, aluminum or glass, and preferably spherically shaped. The particles are preferably provided with a thin coating of silver to facilitate the adhesion of the isotope thereto. Also provided is a tubular ceramic spacer having an axial radiopaque marker therein. The tubular ceramic spacer and radiopaque marker may each be formed from one or two pieces. Where the tubular ceramic spacer and radiopaque marker are formed from two pieces, a first spacer with a first marker therein is press fit into an open end of a first half of the capsule, while a second spacer with a second marker therein is press fit into an open end of a second half of the capsule. The first and second halves of the capsule are then abutted and welded. Where the ceramic spacer and radiopaque marker are each formed from one piece, the spacer, with the marker therein, is press fit partially into the open end of a first half of the capsule, and the open end of the second half of the capsule is then press fit over the remainder of the spacer to abut the first half of the capsule. The two capsule halves are then welded. Alternatively, the open ends of the capsule halves may be thinned and the open end of the second capsule half may be forced over the open end of the first capsule half. The capsule halves may then be joined by welding, swaging, or other means.

Additional objects and advantages of the invention will become apparent to those skilled in the art upon reference to the detailed description taken in conjunction with the provided figures.

BRIEF DESCRIPTION OF THE DRAWINGS

FIG. 1 is an enlarged schematic longitudinal section of a radioactive therapeutic seed according to a first embodiment of the invention;

FIG. 2 is an enlarged schematic longitudinal section of a radioactive therapeutic seed according to a second embodiment of the invention;

FIGS. 4a and 4b are enlarged schematic longitudinal sections of a radioactive therapeutic seed according to alternative fourth embodiments of the invention.

DETAILED DESCRIPTION OF THE PREFERRED EMBODIMENTS

Figure 3:
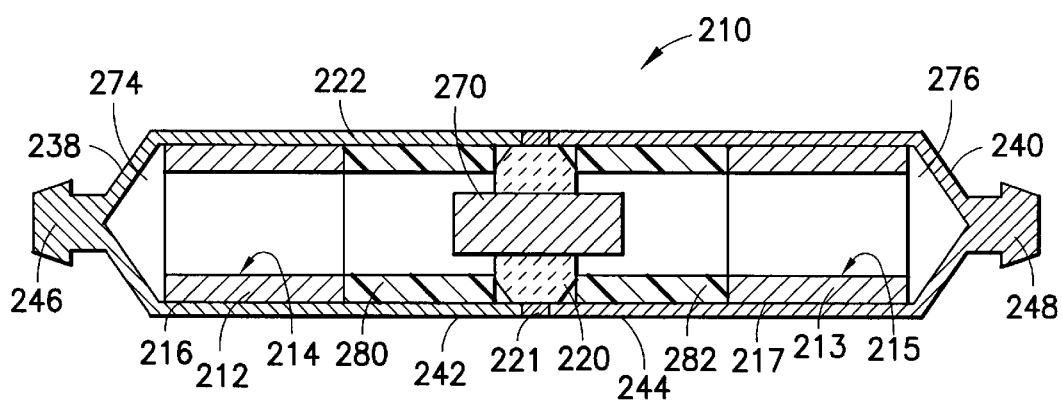
FIG. 3 is an enlarged schematic longitudinal section of a radioactive therapeutic seed according to a third embodiment of the invention.

Referring now to FIG. 1, according to a first embodiment of the invention, a radioactive therapeutic seed 10 includes an inner tube 12 having an inner surface 14 and an outer surface 16 both bearing a radioactive isotope coating 18, a ceramic collar 20 provided about a central portion of the outer surface 16 of the tube 12, a radio-transparent/translucent (low Z) ring or washer 21 provided about a central portion of the ceramic collar 20, and a radio-transparent/translucent (low Z) capsule 22 which abuts the ring 21 and encloses the tube 12 and collar 18.

The inner tube 12 is preferably comprised of titanium, aluminum or other substantially radiolucent material. A silver coating is preferably provided to both the inner and outer surfaces 14, 16 to facilitate and enhance adhesion of the isotope coating 18 thereto. In the preferred embodiment, the isotope 18 does not coat the very end (longitudinal) surfaces 24, 26 of the tube 12 because such a coating has been found to undesirably affect the radiation distribution of the seed 10. The collar 20 is preferably comprised of a ceramic (e.g., alumina or zirconia). If desired, a portion of the collar (e.g., an inner surface, an outer surface, or the ends) may be made from gold which due to its radiopaque properties will act as a marker for the seed. Additionally or alternatively, a portion of the collar 20 may be comprised of a paramagnetic or diamagnetic substance, e.g., a gadolinium metal or salt, to permit visualization of the seed with magnetic resonance imaging (MRI). It is desirable that the collar 20 be tightly formed about the tube 12. The collar 20 is also preferably provided with tapered edges 28, 30 to facilitate movement of the two halves 34, 36, of the capsule 22 over the collar. The ring 21 about the collar 20 is preferably machined or etched from titanium or another radiolucent material, and the capsule halves 34, 36 are preferably machined or etched from an identical material; although, if desired, the capsule halves may be made as drawn tubes which are provided with thick bases (closed ends 38, 40) from which engaging means or connectors can be machined or etched. Thus, each half 34, 36 includes a closed end 38, 40 and an open end 42, 44, respectively; and each closed end 38, 40 is preferably provided with an engaging means or connector 46, 48, described in more detail in previously incorporated U.S. Ser. No. 09/312,215. In assembly, the halves 34, 36 of the capsule 22 are positioned over the tube 12 with the open ends 42, 44 of the halves guided by the tapered edges 28, 30 to form a preferably tight interference fit with the ceramic collar 20. The open ends 42, 44 abut the ring 21 and are butt welded or otherwise welded to the ring 21 to seal the capsule 22 thereby providing the seed with a substantially cylindrical wall of uniform thickness. The ceramic collar 20 protects the contents of the capsule from the heat of welding. For purposes herein, the term "weld" is to be understood in its broadest sense to include any electrical, thermal, or chemical mechanism (or combination thereof) which causes the capsule halves and ring to become integral.

While the ring 21 is shown in FIG. 1 as having the same thickness as the walls of the capsule halves, it will be appreciated that prior to welding, the ring 21 may be thicker and stand proud of the open ends of the capsule halves. It is desirable, however, that upon completion of manufacture, the ring is substantially flush (within 0.003 inches) and integrated with the capsule halves.

Turning now to FIG. 2, a second embodiment of a therapeutic seed 110 according to the invention is shown. The seed 110 includes a preferably titanium capsule 122 defined by two halves 134, 136, each having a closed end 138, 140 provided with an engagement means or connector 146, 148, an open end 142, 144, and an interior portion 174, 176. In the interior portion 174, 176 of each half 134, 136 of the capsule 122, isotope bearing structures 178 spaced by a central ceramic spacer 120 are provided. Preferably, the isotope bearing structures 178 are one or more radiolucent particles, preferably made from titanium, aluminum or glass, and preferably spherically shaped. The particles 178 are provided with a thin coating of silver over which the isotope 118 is provided. The ceramic spacer 120 is a generally hollow cylindrical spacer which carries an axial radiopaque marker 170 therein. A small titanium ring 121 is provided around the central portion of the spacer 120. The spacer 120 preferably includes tapered ends 128, 130 to facilitate positioning the open ends 142, 144 of the capsule thereover. When the open ends 142, 144 of the halves 134, 136 of the capsule are placed over the spacer 120, the ends abut the titanium ring 121 and are welded (in any manner) thereto. The result is a capsule 122 which has a substantially uniform wall thickness.

Referring now to FIG. 3, a third embodiment of a therapeutic seed 210 according to the invention is shown. The seed 210 includes a radiolucent titanium capsule 222 defined by two halves 234, 236, each having a closed end 238, 240 provided with an engagement means 246, 248, an open end 242, 244, and an interior portion 274, 276. In the interior portion 274, 276 of each half 234, 236 of the capsule 222, a silver tube 212, 213 is provided. Each tube 212, 213 is preferably 0.025 inch in length and preferably has a wall thickness of 0.004 inch. The interior surfaces 214, 215 and the exterior surfaces 215, 217 of the tubes are coated with I-125. As the tubes 212, 213 may be shorter than the length of the interior portion 274, 276, a series of spacers 280, 220, 282 may be provided in the interior portion 274, 276 to prevent relative movement of the tubes 212, 213 within the capsule 222. Spacers 280 and 282 may be made of an inexpensive material such as plastic. Spacer 220 is preferably a ceramic spacer in which a radiopaque marker 270 is provided, and over which a titanium ring 221 is provided. Additionally or alternatively, the marker may be diamagnetic. Spacer 220 preferably includes tapered ends 228, 230 to facilitate positioning the open ends 242, 244 of the two halves 234, 236 of the capsule thereover. The two halves 234, 236 of the capsule are positioned to abut the ring 221 and are welded (in any manner) to the ring 221 and about the ceramic spacer 220.

A first alternative fourth embodiment of the invention is seen in FIG. 4a, where therapeutic seed 310a is shown. The seed 310a includes a preferably titanium capsule 322a defined by two halves 334a, 336a, each having a closed end 338a, 340a, an open end 342a, 344a, and an interior portion 374a, 376a. In the interior portion 374a, 376a of each half 334a, 336a of the capsule 322a, isotope bearing structures 378a spaced by a two-piece central ceramic spacer 320a-1, 320a-2 are provided. Preferably, the isotope bearing structures 378a are one or more radiolucent particles, preferably made from titanium, aluminum or glass, and preferably spherically shaped. The particles 378a are provided with a thin coating of silver over which the isotope 318a is provided. The ceramic spacer 320a-1, 320a-2 is a two piece, generally hollow cylindrical spacer which carries a two piece axial radiopaque marker 370a-1, 370a-2 therein. The open end 342a, 344a of each of the halves 334a, 336a of the capsule is press fit over a respective spacer half 320a-1, 320a-2 which is carrying a respective marker half 370a-1, 370a-2 therein so that the open ends of the capsule abut each other. The open ends of the capsule may then be welded (in any manner) to each other. The result is a capsule 322a which has a substantially uniform wall thickness.

A second alternative fourth embodiment of the invention is seen in FIG. 4b, where therapeutic seed 310b is shown.

The seed 310b includes a preferably titanium capsule 322b defined by two halves 334b, 336b, each having a closed end 338b, 340b, an open end 342b, 344b, and an interior portion 374b, 376b. As seen in FIG. 4b, the walls of the open ends 342b, 344b are thin relative to the remainder of the capsule walls. In the interior portion 374b, 376b of each half 334b, 336b of the capsule 322b, isotope bearing structures 378b spaced by a one-piece central ceramic spacer 320b are provided. Preferably, the isotope bearing structures 378b are one or more radiolucent particles, preferably made from titanium, aluminum or glass, and preferably spherically shaped. The particles 378b are provided with a thin coating of silver over which the isotope 318b is provided. The ceramic spacer 320b is a one piece, generally hollow cylindrical spacer which carries a one piece axial radiopaque marker 370b therein. The seed 310b is assembled by press fitting the ceramic spacer 320b over the middle of marker 370b, press fitting capsule half 334b over the tapered end 328b of the spacer 320b, and press fitting capsule half 336b over the remainder of marker 370b such that open end 344b of capsule half 336b extends over open end 342b of capsule half 334b. The open ends of the capsule may then be welded (in any manner) or mechanically swaged to each other. The result is a capsule 322b which has a substantially uniform wall thickness.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciated that certain features of one embodiment may be combined with features of another embodiment to provide yet additional embodiments. In addition, while each capsule is preferably formed from two halves, it will be appreciated that the two parts forming the capsule need not be halves, e.g., one part can be one-third the length of the capsule and the other part can be two-thirds the length of the capsule. Also, while one type of MRI-visible substance has been disclosed, other MRI-visible substances may alternatively be used. Similarly, while two specific ceramics have been disclosed, it will be appreciated that other low-density ceramic materials could be utilized. Likewise, while titanium has been disclosed as the preferred material for the capsule and ring, it will be appreciated that other low-density biocompatible metals could be utilized. Furthermore, while the isotope bearing surface has been disclosed as preferably including both the inner and outer surfaces, it will be appreciated that just the outer surfaces may be used as the isotope bearing surface, though it is believed that the embodiments as described provide the most isotropic radiation distribution. Further yet, while welding has been described as the preferred manner of joining the capsule portions to the ring, it will be appreciated that other manners of sealing such as swaging or providing a shrink-wrap could be utilized. It will therefore be appreciated by those skilled in the art that yet other modifications could be made to the provided invention without deviating from its spirit and scope as so claimed.

What is claimed is:

1. A radioactive therapeutic seed system, comprising:

a plurality of radioactive therapeutic seeds each containing a radioactive isotope, wherein at least one of the therapeutic seeds has a relatively isotropic radiation pattern, and said at least one of the therapeutic seeds has a ceramic collar member.

2. The system according to claim 1, wherein:

said ceramic collar member has a gold or silver portion.

3. The system according to claim 1, wherein:

said collar member includes a portion having an MRI-visible substance.

4. The system according to claim 1, wherein:

said at least one of the therapeutic seeds includes a two part capsule which is sealed together over said ceramic collar.

5. The system according to claim 4, wherein:

said at least one of the therapeutic seeds includes a ring which is sealed together with said two part capsule.

6. The system according to claim 1, wherein:

said at least one of the therapeutic seeds has a two part capsule and a ceramic spacer.

7. The system according to claim 6, wherein:

said at least one of the therapeutic seeds has a metal ring about said ceramic spacer.

8. The system according to claim 1, wherein:

said at least one of the therapeutic seeds has a plurality of radiolucent spacers.

9. The system according to claim 8, wherein:

said at least one of the therapeutic seeds has a radiopaque marker.

10. The system according to claim 8, wherein:

said at least one of the therapeutic seeds has an MRI-visible marker.

* * * * *